US010898253B2

United States Patent
Suddaby

(10) Patent No.: US 10,898,253 B2
(45) Date of Patent: Jan. 26, 2021

(54) ANTERIOR AND LATERAL SPINAL RETRACTOR SYSTEM WITH PIVOTABLE K-WIRE

(71) Applicant: Loubert S. Suddaby, Orchard Park, NY (US)

(72) Inventor: Loubert S. Suddaby, Orchard Park, NY (US)

( * ) Notice: Subject to any disclaimer, the term of this patent is extended or adjusted under 35 U.S.C. 154(b) by 30 days.

(21) Appl. No.: 16/274,661

(22) Filed: Feb. 13, 2019

(65) Prior Publication Data
US 2020/0253657 A1 Aug. 13, 2020

(51) Int. Cl.
| | | |
|---|---|---|
| A61B 17/88 | (2006.01) | |
| A61B 17/02 | (2006.01) | |
| A61B 17/17 | (2006.01) | |
| A61B 17/70 | (2006.01) | |
| A61B 1/32 | (2006.01) | |

(52) U.S. Cl.
CPC ............ *A61B 17/8897* (2013.01); *A61B 1/32* (2013.01); *A61B 17/0206* (2013.01); *A61B 17/1757* (2013.01); *A61B 17/7074* (2013.01); *A61B 17/0218* (2013.01); *A61B 2017/0256* (2013.01)

(58) Field of Classification Search
CPC ....... A61B 17/86; A61B 17/84; A61B 17/842; A61B 17/844; A61B 17/846; A61B 17/848; A61B 17/8897; A61B 17/0206; A61B 1/32; A61B 17/1757; A61B 17/7074; A61B 17/7076; A61B 17/7079; A61B 17/0218; A61B 2017/0256; A61B 17/7077
See application file for complete search history.

(56) References Cited

U.S. PATENT DOCUMENTS

| | | | | |
|---|---|---|---|---|
| 6,083,154 A | * | 7/2000 | Liu ..................... | A61B 17/0293 600/231 |
| 6,139,493 A | * | 10/2000 | Koros ................ | A61B 17/0206 600/213 |
| 8,152,720 B2 | | 4/2012 | Loftus et al. | |
| 8,246,538 B2 | | 8/2012 | Gorek | |
| 8,357,184 B2 | | 1/2013 | Woolley et al. | |
| 8,376,940 B2 | | 2/2013 | Gorek | |
| 8,435,269 B2 | | 5/2013 | Woolley et al. | |
| 8,535,320 B2 | | 9/2013 | Woolley et al. | |
| 8,617,063 B2 | | 12/2013 | Loftus et al. | |
| 8,852,089 B2 | * | 10/2014 | Blackwell .......... | A61B 17/0206 600/210 |
| 9,050,146 B2 | | 6/2015 | Woolley et al. | |
| 9,307,972 B2 | | 4/2016 | Lovell et al. | |
| 9,554,833 B2 | | 1/2017 | Woolley et al. | |
| 9,795,370 B2 | | 10/2017 | O'Connell et al. | |
| 9,962,147 B2 | | 5/2018 | O'Connell et al. | |
| 10,172,601 B2 | * | 1/2019 | Ahn ....................... | A61B 17/02 |

(Continued)

FOREIGN PATENT DOCUMENTS

| | | | | |
|---|---|---|---|---|
| EP | 3403589 A1 | * 11/2018 | ............. | A61B 17/02 |
| WO | WO-2010121291 A1 | * 10/2010 | ......... | A61B 17/1757 |

*Primary Examiner* — Matthew J Lawson
(74) *Attorney, Agent, or Firm* — Simpson & Simpson, PLLC; Michael Nicholas Vranjes

(57) ABSTRACT

A pivotable wire assembly, including a pivotable wire, including a first section having a first end and a second end, a pivotable section, and a second section connected to the second end via the pivotable section, the second section having an engaging portion, wherein the first section is pivotably displaceable relative to the second section.

22 Claims, 12 Drawing Sheets

(56) References Cited

U.S. PATENT DOCUMENTS

| | | | |
|---|---|---|---|
| 2004/0172039 A1* | 9/2004 | Dye | A61B 17/1746 606/99 |
| 2006/0189848 A1* | 8/2006 | Penenberg | A61B 1/32 600/210 |
| 2008/0114363 A1* | 5/2008 | Chin | A61B 17/842 606/241 |
| 2009/0187194 A1* | 7/2009 | Hamada | A61B 17/8897 606/104 |
| 2012/0271120 A1* | 10/2012 | Seex | A61B 17/02 600/235 |
| 2013/0123852 A1* | 5/2013 | Sandhu | A61B 17/7077 606/264 |
| 2013/0317312 A1 | 11/2013 | Eastlack et al. | |
| 2015/0230785 A1* | 8/2015 | DeVere, Jr. | A61B 1/32 600/213 |
| 2017/0105770 A1 | 4/2017 | Woolley et al. | |
| 2017/0150955 A1* | 6/2017 | Williams | A61B 5/0488 |
| 2017/0231664 A1 | 8/2017 | Doose et al. | |
| 2018/0153585 A1 | 6/2018 | Levine | |
| 2018/0206833 A1 | 7/2018 | O'Connell et al. | |
| 2019/0076172 A1* | 3/2019 | Sandhu | A61B 17/88 |
| 2020/0129168 A1* | 4/2020 | Reitblat | A61B 17/846 |

* cited by examiner

ANTERIOR AND LATERAL SPINAL RETRACTOR SYSTEM WITH PIVOTABLE K-WIRE

FIELD

The present disclosure relates to the field of orthopedic surgery, and more particularly to surgical retractor systems, and even more particularly, to spinal retractor systems using a pivotable wire for mounting the retractor blade.

BACKGROUND

Successful surgical procedures are heavily dependent on the ability of the surgeon to visualize the target area either directly or indirectly via fluoroscopy or endoscopy. Much of spinal surgery is still heavily dependent on direct vision by the surgeon's eyes, necessitating a wide variety of surgical retractor systems which function to displace intervening tissue and maintain displacement such that surgery can be performed on a target area (disc, vertebrae, neural tissue).

Retracted tissue exerts counter pressure on any blades, arms, or probes inserted to spread and displace intervening tissue layers. Most retractor systems utilize blades that are displaced by ratcheting mechanisms that they are fixedly attached to. As the blades spread apart with greater force, tissue counter pressure increases causing untoward consequences. Greater forces causes blades to flex such that they are held apart adequately at the surface of the wound, but the distal tips do not move apart to the same degree, unless the retractor blades are very thick and robust, which compromises insertion of the blades themselves along with visualization. Additionally, the flex in the blades increases as the surface ratcheting mechanism separates the blades, creating a tendency for the blade to eject from the wound itself. Even minor degrees of ejection allow tissue to creep under the blade tips and compromise the field of view or place sensitive tissue in harm's way.

The longer the retractor blades are, the more difficult it is to retract the distal tips with a perpendicular surface force because of the longer lever arm associated with longer blades. If it is required that the distal tips diverge for visualization, the problem of spreading the blades is exacerbated even further.

To mitigate these issues, retractor systems have been devised to allow the blades to "toe out" or diverge distally after insertion by pivotal attachment of the retractor assembly on the surface. Anchoring pins have also been used to prevent retractor expulsion. To address both issues, complex and expensive systems have been developed to allow good visualization of target areas in deep wounds with limited success.

Thus, there is a long felt need for an improved spinal retractor system wherein individual retractor blades are initially anchored to the spine with joined linear anchors such that the anchor joint serves as a polyaxial focal attachment point for the blade to the spine, thereby permitting an infinite number of orienting angles and positions of the blade to permit tissue retraction.

Additionally, Kirschner wires or K-wires or pins are sterilized, sharpened, smooth stainless steel pins. Introduced in 1909 by Martin Kirschner, the wires are now widely used in orthopedics and other types of medical and veterinary surgery. They come in different sizes and are used to hold bone fragments together (pin fixation) or to provide an anchor for skeletal traction. The pins are often driven into the bone through the skin (percutaneous pin fixation) using a power or hand drill. They also form part of the Ilizarov apparatus. K-wires are used for temporary fixation during some operations. After definitive fixation they are then removed. The pins are usually removed four weeks post operation. K-wires can be used for definitive fixation if the fracture fragments are small (e.g., wrist fractures and hand injuries). In some settings they can be used for intramedullary fixation of bones such as the ulna. Tension band wiring is a technique in which the bone fragments are transfixed by K-wires which are then also used as an anchor for a loop of flexible wire. As the loop is tightened the bone fragments are compressed together. Fractures of the kneecap and the olecranon process of the elbow are commonly treated by this method. A wire is passed through the skin then transversely through the bone and out the other side of the limb. The wire is then attached to some form of traction so that the pull is applied directly to bone. In traction of the femur for example, the protruding ends of the wire are fixed to the legs of a horseshoe shaped frame which maintains tension in the wire while the crook of the horseshoe is attached via line and pulleys to weights which maintain the traction. K-wires can be used for temporary joint immobilization. K-wires can be used to guide cannulated screws to a precise location. However, K-wires known in the art do not provide for both an engaging portion and a pivoting portion such that it can be used to pivotably mount a retractor blade.

Thus, there is also a long felt need for a K-wire having an engaging portion and a pivoting portion such that a K-wire may be used to pivotably mount a retractor blade.

SUMMARY

According to aspects illustrated herein, there is provided a pivotable wire assembly, comprising a pivotable wire, including a first section having a first end and a second end, a pivotable section, and a second section connected to the second end via the pivotable section, the second section having an engaging portion, wherein the first section is pivotably displaceable relative to the second section.

According to aspects illustrated herein, there is provided a retractor blade assembly, comprising a retractor blade, including a blade portion having a first end, a second end, and a hole, and a handle portion connected to the blade portion proximate the first end, and a pivotable wire operatively arranged to engage the hole, the pivotable wire including a first section having a third end and a fourth end, a pivotable section, and a second section connected to the fourth end via the pivotable section, the second section having an engaging portion, wherein the first section is pivotably displaceable relative to the second section.

The present disclosure comprises an improved spinal retractor system wherein individual retractor blades are initially anchored to the spine with jointed linear anchors such that the anchor joint, or swivel, serves as a polyaxial focal attachment point for the blade to the spine, thereby permitting an infinite number of orienting angles and positions of the blade to permit tissue retraction. The blades, in turn, are adjustable in length, have a built-in track to accommodate the linear swivel anchor and are attachable to any of a variety of existing internal platforms that attach to operating tables or can be separated by a ratcheting framework to serve as a free-standing retractor anchored to the spine.

The present disclosure broadly discloses a retractor system that is simple to insert and activate. While most systems displace blade tips by activation of a crank and ratchet system at wound surface, the present disclosure places the blade tips in their ideal location first, anchors them and then displaces the proximal ends after ideal placement has already been secured. A system and method operatively conceived in a fashion diametrically opposite to conventional devices. Since the mechanical advantage is greater to displace blades at the surface of the wound closest to the crank/ratcheting spreading mechanism, far less force is needed, and ideal distal visualization based on retractor tip location is always assured. Furthermore, by having blades that are adjustable in length, the number of different blade lengths in a given system is substantially reduced.

To achieve these ends, a retractor blade is chosen and placed into a wound, (lateral) and observed under fluoroscopy. Said retractor has a tissue blade with a blunt contoured tip permitting it to be pushed against the spine displacing but not transecting tissue. It is placed in line with psoas fibers pressed against the spine and then rotated to displace the psoas tissues, remaining intimately in contact with the surface of the vertebra. The tip of the retractor is then moved cranially or caudally along the spine until the ideal tip position is observed on fluoroscopy. The retractor tip is then anchored to the vertebra by a threaded anchor which is slid down a sleeve enclosed in the retractor blade. The anchor has a swivel connection or universal joint at a point just proximal to the anchoring threads such that when the threads are fully engaged in the vertebra, the swivel point is right at the surface of the vertebra. The swivel joint permits hinged, limited polyaxial movement, or full polyaxial movement depending upon the surgeon's need or anatomical issues. As the anchor threads into the vertebra, it secures the retractor blade tip to the spine in an intimate fashion but allows the blade to be oriented at any angle while remaining securely attached to the spine, thereby maintaining ideal placement and thwarting tissue creep beneath the tip. The retractor blade's proximal portion is then displaced away from the incision and anchored to a Bookwalter® O-ring retractor system to maintain amore perpendicular attitude with the spine.

A second retractor blade is anchored to an adjacent vertebra in a similar fashion and rocked back to a perpendicular attitude and anchored to the Bookwalter® O-ring retractor system across from the first retractor blade. Other retractor blades can be added as needed to improve visualization by anchoring to other parts of the exposed vertebrae or to the disc itself both anteriorly and posteriorly to provide for circumferential retraction and tissue protection.

Since the tips of the retractors are anchored prior to tissue retraction, ideal distal visualization is always maintained. Furthermore, since retraction force is utilized only to displace the proximal portion of the retractor blades, mechanical advantage is maximized. The blade tip is secured to the spine in a polyaxial or limited polyaxial fashion, which allows an infinite number of retractor blade orientations to be achieved. For example, if a pure hinge connection is utilized, the retractor blade will displace proximally in a direction determinedly by the distal hinge orientation, which in turn is adjustable by simply turning the hinged anchor. Furthermore, by having adjustable blade lengths, the total number of blades required is dramatically reduced.

It is an object of the present disclosure to provide for a spinal tissue retraction system that is inexpensive, easy to deploy, and provides superior visualization of targeted surgical loci than all systems presently in existence.

It is also an object of the present disclosure to have a spinal retraction system that is compatible with existing frame-based systems already in use.

It is also an object of the present disclosure to have the retractor function entirely independent of existing frame-based systems and function entirely attached to the spine itself, without need for attachment to the operating room table, if desired.

It is also an object of the present disclosure that the spinal tissue retraction system be compatible with existing light sources to provide for ideal visualization of the surgical sites so exposed.

Additionally, it is an object of the present disclosure that the component parts are so simple and inexpensive to be produced that the retractor system is entirely disposable thereby negating the need for washing, cleaning, and storage as well as mitigating the risk of disease transmittal.

The present disclosure comprises a system that is far simpler than existing spinal retraction systems and lends itself to retraction in surgical procedures outside of spine. The principle difference from existing systems is the ability to ideally place and anchor the blade tip prior to activation of the retractor mechanism. Indeed, the system is so simple a ratcheting crank mechanism is not necessary since the blade can simply be attached to a table mounted O retractor thereby obviating the need for a mechanical retractor displacement device of any description.

In some embodiments, the cranial and caudal blade tips comprise a concave contour mimicking the curved contour of the spinal vertebrae to allow for a more intimate tip to bone surface contact to prevent tissue creep beneath the blade tip.

In some embodiments, the blade comprises two components that are slidably connected to allow the length of the blade to be adjusted. Such feature allows the user to adjust individual wound depths such that multiple retractor blades are not needed.

In some embodiments, the blade comprises a detatachable handle to allow blade placement in the wound, said wound handle serving as an attachment to a table mounted O ring retractor system, or detached to permit connecting of the blade to a free-floating crank ratcheting expansion platform.

In some embodiments, each blade comprises at least one linear sleeve permitting placement of a hinged or polyaxial swivel anchor to fixate the blade. In some embodiments, each blade comprises at least one port for placement of an external light source for wound visualization.

For systems having an O ring attachment, the handle of the blade (affixed at roughly a right angle) will affix to the O ring perimeter. The handle, like the blade, will be adjustable in length to accommodate for variations in O ring position. Both blade length and handle length will be adjustable and securable once appropriate lengths are achieved.

For systems no using a table mounted O ring, the blade handles will be removed once the blades are secured to an independent crank ratcheting assembly designed to displace the proximal ends of the blades at or external to the wound surface.

A key factor to allow such flexibility in blade placement, fixation, and expansion is the ability to anchor the blade in a hingeable fashion at the level of the spine. This provides for significant technical and mechanical advantage not only in blade placement, but also in blade displacement once the tips are anchored. Existing anchors are not jointed and simply bend at the surface of the spine when blades are displaced with force, thereby increasing the probability of anchor breakage and decreasing the ability to achieve optimal visualization.

Once the blade tip is optimally placed under fluoroscopic visualization, a swivel anchor is slid down a channel fixed to or contained in the blade along the blade length. In some embodiments, the portion of the anchor distal to the swivel connection is threaded and the anchor is screwed into the bone until the swivel point is at or near the bone surface. The swivel itself will engage a lip in the channel at the distal point of the blade such that, as the anchor is screwed into the bone it will draw the blade tip in a position intimately juxtaposed to the spine surface. The swivel component will be situated such that full or limited polyaxial movement occurs at the spine/retractor interface. This feature permits both securement of the retractor blade tip to the spine to mitigate displacement and tissue creep while permitting an infinite number of angles for final blade placement.

When a second retractor is placed in a second position opposite the first retractor and the proximal ends of the blades are displaced, the retractor blades mirror each other in a traction and counter traction fashion such that a balanced force is placed on the O ring or retractor ratcheting mechanism, regardless of which system is chosen.

In some embodiments, both the blade and the handle lengths area adjustable. Optimal visualization is obtained once the light source is added. In some embodiments, the blades comprise metal or hard plastics such as polycarbonates. In some embodiments, the anchor pins comprise metal, at least at the tip which engages bone.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

By "non-rotatably connected" elements, we mean that: the elements are connected so that whenever one of the elements rotate, all the elements rotate; and relative rotation between the elements is not possible. Radial and/or axial movement of non-rotatably connected elements with respect to each other is possible, but not required. By "rotatably connected" elements, we mean that the elements are rotatable with respect to each other.

Figure 1:
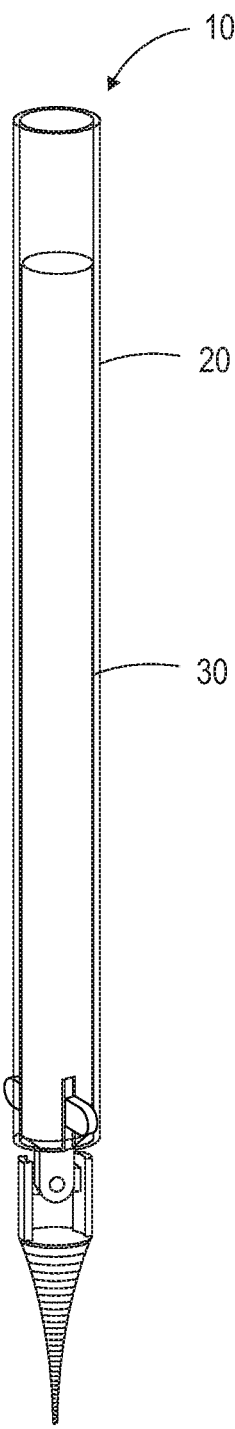
FIG. 1 is a perspective view of a pivotable wire assembly.
Figure 2:
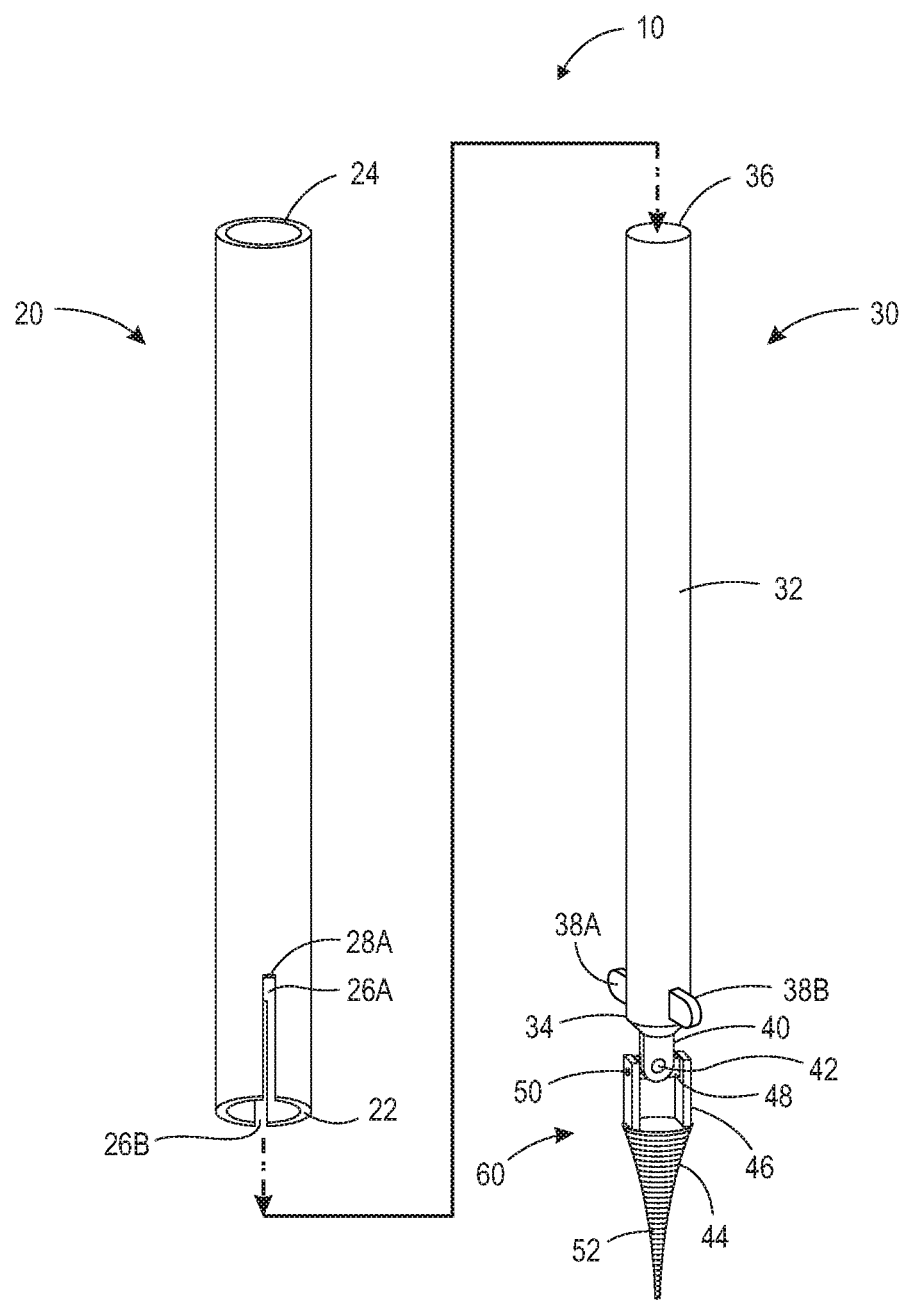
FIG. 2 is an exploded perspective view of the pivotable wire assembly shown in FIG. 1.

Referring now to the figures, FIG. 1 is a perspective view of pivotable wire assembly 10. FIG. 2 is an exploded perspective view of pivotable wire assembly 10. Wire assembly 10 generally comprises sheath 20 and a pivotable wire, for example, pivotable wire 30, 130, 230, 330. It should be appreciated that although FIGS. 1 and 2 show pivotable wire 30 in wire assembly 10, pivotable wires 130, 230, and 330 may be used instead. In some embodiments, pivotable wires 30, 130, 230, and 330 are K-wires or Steinmann (or intramedullary) pins. The following description should be read in view of FIGS. 1 and 2.

Sheath 20 comprises end 22, end 24, and one or more slots (e.g., slots 26A-26B). As shown, sheath 20 is a tube and may be rigid, partially rigid, or flexible. In some embodiments, sheath 20 comprises a polymer or plastic. Slots 26A and 26B comprise edges 28A and 28B (not shown), respectively. Slots 26A and 26B are operatively arranged to engage one or more protrusions on the pivotable wire, as will be discussed in greater detail below.

Pivotable wire (or K-wire) 30 comprises section 32, section 44, and pivotable section 60. Section 32 is generally cylindrical and includes end 34 and end 36. Section 32 further comprises one or more protrusions (e.g., protrusions 38A-B) arranged proximate end 34. Protrusions 38A-B are operatively arranged to engage slots 26A-B such that end 22 of sheath 20 extends down over pivotable section 60 and at least partially over section 44. In some embodiments, when sheath 20 is fully engaged with pivotable wire 30, edges 28A-B abut against or are arranged substantially proximate to protrusions 38A-B. As such, section 32 and section 44 remain substantially concentrically aligned while pivotable wire 30 is rotated or thrusted to engage or impale engaging portion 52 into bone or tissue. Once engaging portion 52 is sufficiently engaged with the bone or tissue, sheath 20 is removed from pivotable wire 30, or displaced back toward end 36 of pivotable wire 30, such that section 32 may pivotably displace relative to section 44 and/or engaging portion 52. Section 32 further comprises fork 40 connected to end 34. Fork 40 generally comprises two flanges and a through-bore therethrough and is hingedly connected to center block 48 via pin 42. In some embodiments, fork 40 is non-rotatably connected to end 34. In some embodiments, fork 40 is rotatably connected to end 34.

Section 44 is connected to section 32 via pivotable section 60. In the embodiment shown, pivotable section 60 is a universal joint (i.e., a shaft coupling capable of transmitting rotation from one shaft to another shaft not collinear with it). Section 44 comprises fork 46 and engaging portion 52. Fork 46 generally comprises two flanges and a through-bore therethrough and is hingedly connected to center block 48 via pin 50. In some embodiments, engaging portion 52 is non-rotatably connected to fork 46. In some embodiments, engaging portion 52 is rotatably connected to fork 46.

Engaging portion 52 is operatively arranged to be connected to bone or tissue. Engaging portion 52 may be, for example, threaded such that as it can be screwed into bone or tissue. In some embodiments, engaging portion 52 is a thin sharp wire that can be thrust into the bone using force.

Figure 3:
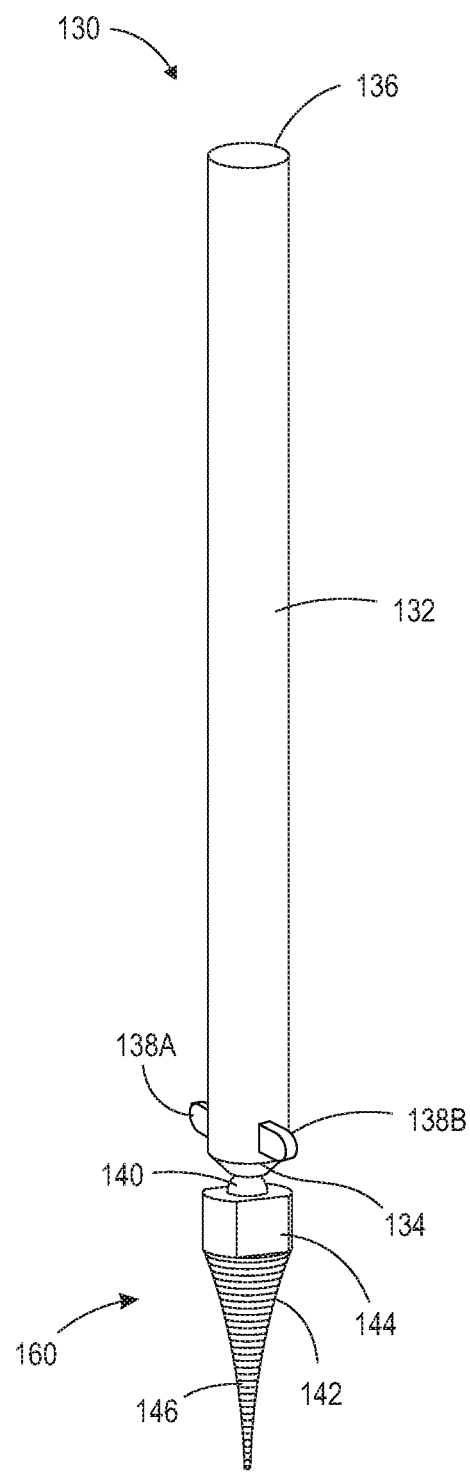
FIG. 3 is a perspective view of a pivotable wire.

FIG. 3 is a perspective view of pivotable wire 130. Pivotable wire (or K-wire) 130 comprises section 132, section 142, and pivotable section 160. Section 132 is generally cylindrical and includes end 134 and end 136. Section 132 further comprises one or more protrusions (e.g., protrusions 138A-B) arranged proximate end 134. Protrusions 138A-B are operatively arranged to engage slots 26A-B such that end 22 of sheath 20 extends down over pivotable section 160 and at least partially over section 142. In some embodiments, when sheath 20 is fully engaged with pivotable wire 130, edges 28A-B abut against or are arranged substantially proximate to protrusions 138A-B. As such, section 132 and section 142 remain substantially concentrically aligned while pivotable wire 130 is rotated or thrusted to engage or impale engaging portion 146 into bone or tissue. Once engaging portion 146 is sufficiently engaged with the bone or tissue, sheath 20 is removed from pivotable wire 130, or displaced back toward end 136 of pivotable wire 130, such that section 132 may pivotably displace relative to section 142 and/or engaging portion 146. Section 132 further comprises ball 140 connected to end 134. Ball 140 is at least partially rounded, for example, a spherical, a cylindrical, or other curvilinear shape, and is arranged to pivotably engage with and connect to socket 144. In some embodiments, ball 140 is non-rotatably connected to end 134.

Section 142 is connected to section 132 via pivotable section 160. In the embodiment shown, pivotable section 160 is a ball and socket joint (i.e., a joint in which a ball moves within a socket so as to allow rotary motion in every direction within certain limits). Section 142 comprises socket 144 and engaging portion 146. Socket 144 generally comprises an at least partially rounded inner surface, for example, a spherical, a cylindrical, or other curvilinear shape, and is arranged to pivotably engage with, and axially retain, ball 140. Section 142 may further comprise an enclosure plate arranged to axially secure ball 140 to socket 144. In some embodiments, engaging portion 146 is non-rotatably connected to socket 144. In some embodiments, engaging portion 146 is rotatably connected to socket 144. In some embodiments, section 132 comprises the socket and section 142 comprises the ball.

Engaging portion 146 is operatively arranged to be connected to bone or tissue. Engaging portion 146 may be, for example, threaded such that as it can be screwed into bone or tissue. In some embodiments, engaging portion 146 is a thin sharp wire that can be thrust into the bone using force. In some embodiments, section 142 is capable of being rotatably locked with section 132.

Figure 4:
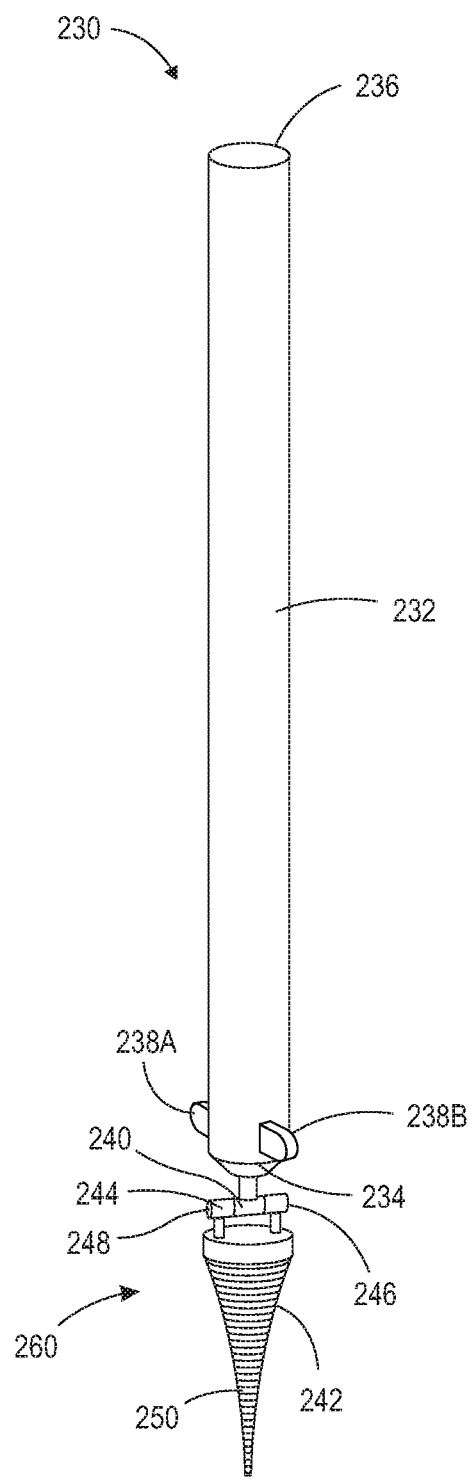
FIG. 4 is a perspective view of a pivotable wire.

FIG. 4 is a perspective view of pivotable K-wire 230. Pivotable wire (or K-wire) 230 comprises section 232, section 242, and pivotable section 260. Section 232 is generally cylindrical and includes end 234 and end 236. Section 232 further comprises one or more protrusions (e.g., protrusions 238A-B) arranged proximate end 234. Protrusions 238A-B are operatively arranged to engage slots 26A-B such that end 22 of sheath 20 extends down over pivotable section 260 and at least partially over section 242. In some embodiments, when sheath 20 is fully engaged with pivotable wire 230, edges 28A-B abut against or are arranged substantially proximate to protrusions 238A-B. As such, section 232 and section 242 remain substantially concentrically aligned while pivotable wire 230 is rotated or thrusted to engage or impale engaging portion 250 into bone or tissue. Once engaging portion 250 is sufficiently engaged with the bone or tissue, sheath 20 is removed from pivotable wire 230, or displaced back toward end 236 of pivotable wire 230, such that section 232 may pivotably displace relative to section 242 and/or engaging portion 250. Section 232 further comprises knuckle 240 connected to end 234. Knuckle 240 generally comprises a tube having a through-bore. In some embodiments, knuckle 240 is non-rotatably connected to end 234. In some embodiments, knuckle 240 is rotatably connected to end 234.

Section 242 is connected to section 232 via pivotable section 260. In the embodiment shown, pivotable section 260 is a hinge joint (i.e., a jointed or flexible device on which a swinging part turns). Section 242 comprises knuckles 244 and 246, and engaging portion 250. Knuckles 244 and 246 are connected to engaging portion 250. Knuckle 244 generally comprises a tube having a through-bore and knuckles 246 generally comprises a tube having a through-bore. The tubes of knuckles 240, 244, and 246 are aligned and connected via pin 248 as shown in FIG. 4, thereby forming a hinged connection between section 232 and 242. In some embodiments, engaging portion 250 is non-rotatably connected to knuckles 244 and 246. In some embodiments, engaging portion 250 is rotatably connected to knuckles 244 and 246. In some embodiments, section 232 comprises two knuckles and section 242 comprises one knuckle. In some embodiments, one or more knuckles are used (e.g., five knuckles with two knuckles connected to section 232 and three knuckles connected to section 242).

Engaging portion 250 is operatively arranged to be connected to bone or tissue. Engaging portion 250 may be, for example, threaded such that as it can be screwed into bone or tissue. In some embodiments, engaging portion 250 is a thin sharp wire that can be thrust into the bone using force.

Figure 5:
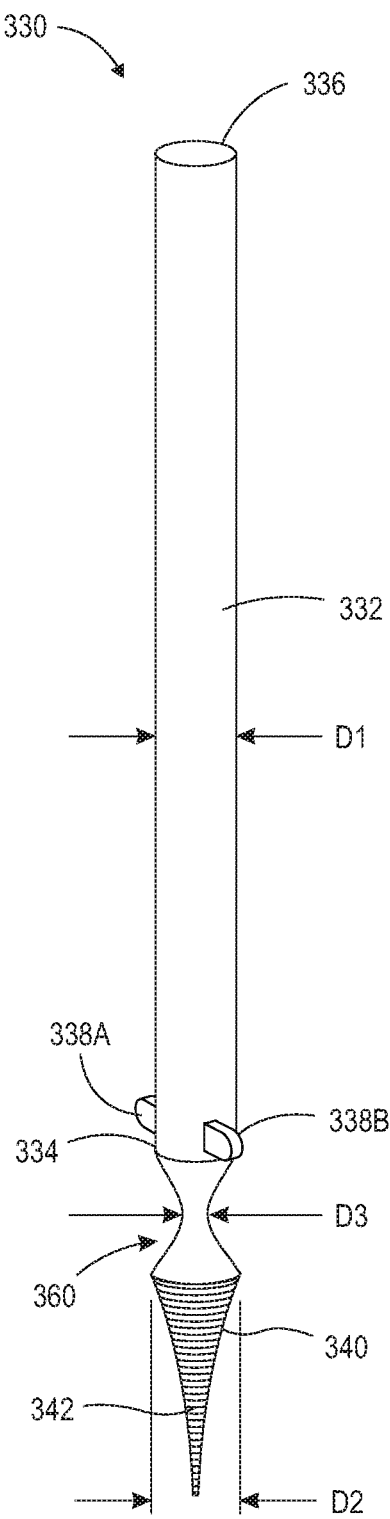
FIG. 5 is a perspective view of a pivotable wire.

FIG. 5 is a perspective view of pivotable K-wire 330. Pivotable wire (or K-wire) 330 comprises section 332, section 340, and pivotable section 360. Section 332 is generally cylindrical and includes end 334 and end 336. Section 332 further comprises one or more protrusions (e.g., protrusions 338A-B) arranged proximate end 334. Protrusions 338A-B are operatively arranged to engage slots 26A-B such that end 22 of sheath 20 extends down over pivotable section 360 and at least partially over section 340. In some embodiments, when sheath 20 is fully engaged with pivotable wire 330, edges 28A-B abut against or are arranged substantially proximate to protrusions 338A-B. As such, section 332 and section 340 remain substantially concentrically aligned while pivotable wire 330 is rotated or thrusted to engage or impale engaging portion 342 into bone or tissue. Once engaging portion 342 is sufficiently engaged with the bone or tissue, sheath 20 is removed from pivotable wire 330, or displaced back toward end 336 of pivotable wire 330, such that section 332 may pivotably displace relative to section 340 and/or engaging portion 342.

Section 340 is connected to section 332 via pivotable section 360. In the embodiment shown, pivotable section 360 is a thinned section of pivotable wire 330. For example, section 332 comprises diameter D1, section 342 comprises diameter D2, and pivotable section 360 comprises diameter D3, wherein diameter D3 is less than diameter D1 and diameter D2. In some embodiments, section 332, section 340, and pivotable section 360 are integrally formed with the diameter of pivotable section 360 being less than the diameter of sections 332 and 340. Once section 340 is engaged in bone or tissue, the thinned diameter of pivotable section 360 allows section 332 to pivotably displace relative to section 340 proximate the engagement point. Section 340 comprises engaging portion 342. In some embodiments, engaging portion 342 is non-rotatably connected to pivotable section 360. In some embodiments, engaging portion 342 is rotatably connected to pivotable section 360. In some embodiments, diameter D3 is equal to diameters D1 and D2, and due to the malleability of pivotable wire 330, specifically section 360, section 332 is capable of pivotably displacing relative to section 340 (i.e., section 360 does not need to be "thinned").

Engaging portion 342 is operatively arranged to be connected to bone or tissue. Engaging portion 342 may be, for example, threaded such that as it can be screwed into bone or tissue. In some embodiments, engaging portion 342 is a thin sharp wire that can be thrust into the bone using force.

Figure 6:
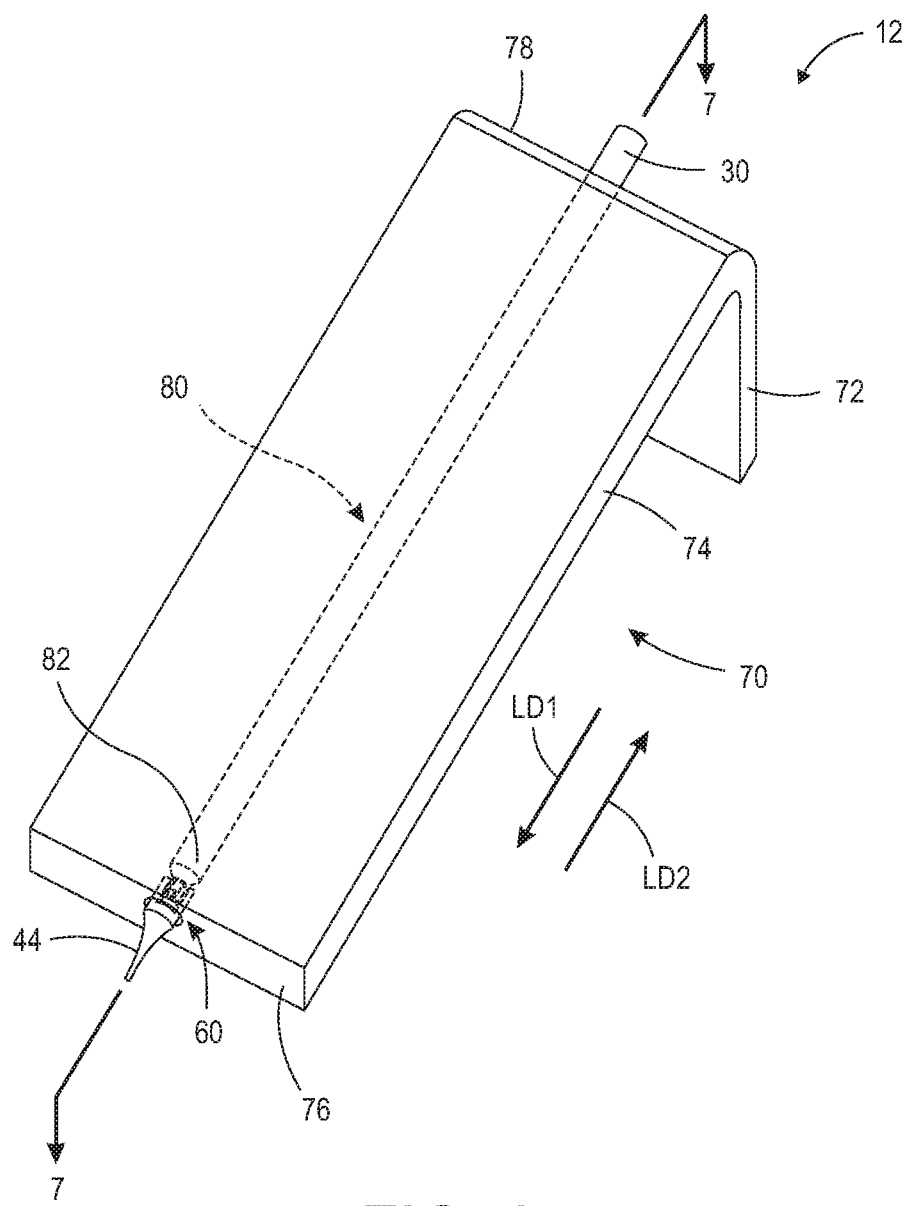
FIG. 6 is a perspective view of a retractor blade assembly.
Figure 7:
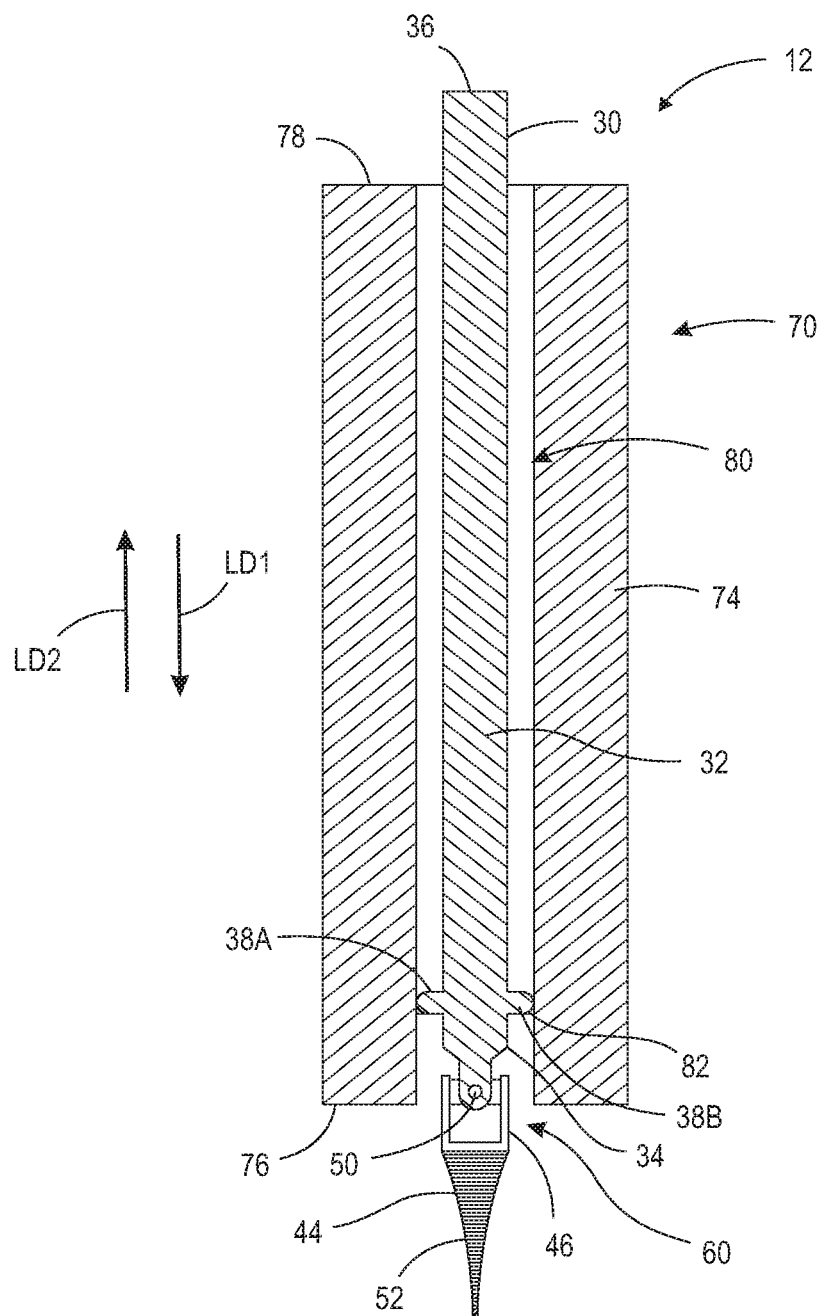
FIG. 7 is a cross-sectional view of the retractor blade assembly taken generally along line 7-7 in FIG. 6.

FIG. 6 is a perspective view of retractor blade assembly 12. FIG. 7 is a cross-sectional view of retractor blade assembly 12 taken generally along line 7-7 in FIG. 6. Retractor blade assembly 12 generally comprises retractor blade 70 and a pivotable wire, for example, pivotable wire 30, 130, 230, 330. It should be appreciated that although FIGS. 6 and 7 show pivotable wire 30 in retractor blade assembly 12, pivotable wires 130, 230, and 330 may be used instead. The following description should be read in view of FIGS. 6 and 7.

Retractor blade 70 comprises handle portion 72 and blade portion 74. Blade portion 74 comprises end 76 and end 78. Handle portion 72 is connected to blade portion 74 proximate end 78. In some embodiments, handle portion 72 is removably connected to blade portion 74. Blade portion 74 further comprises hole 80. In some embodiments, hole 80 is a through-bore which extends from end 78 to end 76. In some embodiments, hole 80 is a channel arranged in blade portion 74 which extends from end 78 to end 76. In some embodiments, hole 80 is a through-bore which extends from a point between end 78 and end 76, to end 76. In some embodiments, hole 80 is a channel arranged in blade portion 74 which extends from a point between end 78 and end 76, to end 76. Blade portion 74 further comprises flange 82 proximate end 76. As shown in FIG. 7, flange 82 reduces the diameter of hole 80 in order to engage protrusions 38A-B. Specifically, as pivotable wire 30 is inserted into hole 80 from end 78 in longitudinal direction LD1, flange 82 allows section 44 and pivotable section 60 to extend at least partially out of hole 80 beyond end 76, but allows only a portion of section 32 to do the same. As such, retractor blade 70, like section 32, is arranged to pivotably displace relative to section 44 and/or engaging portion 52. In some embodiments, retractor blade 70 comprises polycarbonate. In some embodiments, and as shown in FIG. 7, end 76 of retractor blade 70 is aligned with pivotable section 60 so that when section 44 and/or engaging portion 52 is engaged into disc or bone, retractor blade 70 (specifically end 76) is held in firm apposition to the spine. This is to prevent tissue creep beneath end 76 of retractor blade 70 and consequent injury of retracted tissues from sharp surgical instruments. By firmly securing (e.g., screwing or impaling) section 44 and/or engaging portion 52 into bone or cartilage, it can firmly appose retractor blade 70 to the spine, but simultaneously allow infinite angle changes in retractor blade 70 by virtue of the swivel while preventing tissue creep beneath the blade which is common in present systems and aggravating as well as hazardous. In some embodiments, a plurality of pivotable wires are used, if desired, to fixate retractor blade 70 more securely, or to fixate end 76 in a particular rotator orientation referable to the vertical axis. In this regard, retractor blade 70 would or could have a plurality of holes (e.g., holes similar to or identical to hole 80) to engage such fixations or pivotable wires. For example, two pivotable wires (e.g., pivotable wires 30) may be fed down two separate holes (e.g., holes 80) and secured to a vertebra, which would provide greater stabilization and securement to the retractor blade (e.g., retractor blade 70), and limit the angular movement or rotation of the retractor blade.

FIGS. 6 and 7 show pivotable wire 30 in a fully engaged position relative to retractor blade 70. By fully engaged, it is meant that pivotable section 60 and section 44 extend completely beyond end 76. The fully engaged position should be used after engaging portion 52 has been secured to the bone or tissue during the pivoting of retractor blade 70. However, during engagement (i.e., as engaging portion 52 is being secured to the bone or tissue), it may be desirable that pivotable section 60 and at least a portion of section 44 remain within hole 80 such that section 32 and section 44 remain substantially concentrically aligned. Engaging portion 52 may be secured to the bone or tissue with greater ease if it is not pivotably displaced with respect to section 32 (e.g., if engaging portion 52 is being screwed or thrusted into the bone or tissue). Once engaging portion 52 is secured to the bone or tissue, retractor blade 70 pulled back or displaced in longitudinal direction LD2 relative to pivotable wire 30 thereby exposing section 44 and pivotable section 60.

Figure 8:
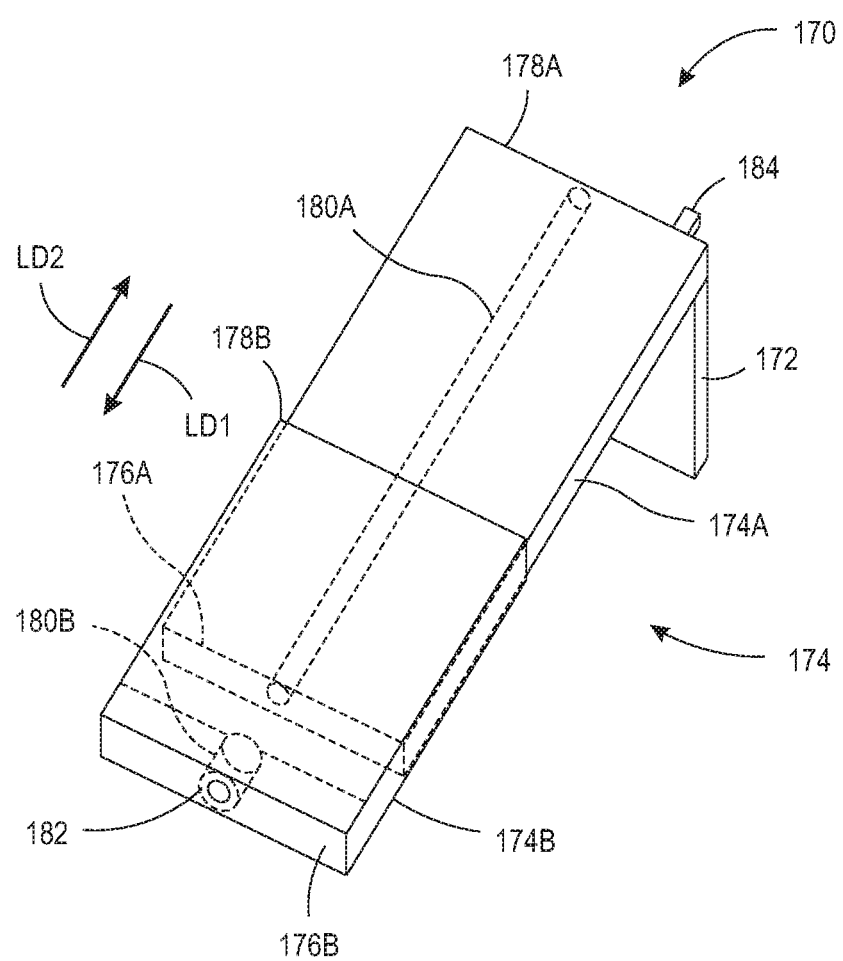
FIG. 8 is a perspective view of a retractor blade.

FIG. 8 is a perspective view of retractor blade 170. Retractor blade 170 comprises handle portion 172 and blade portion 174. In some embodiments, blade portion 174 is telescoping and comprises blade portion 174A and blade portion 174B. The telescoping engagement of blade portion 174A and blade portion 174B allows the length of blade portion 174 to be adjusted. It should be appreciated that although FIG. 8 only shows two blade portions, any suitable number of telescoping blade portions may be used.

Blade portion 174A comprises end 176A and end 178A. Handle portion 172 is connected to blade portion 174A proximate end 178A. In some embodiments, handle portion 172 is removably connected to blade portion 174A. Blade portion 174A further comprises hole 180A. In some embodiments, hole 180A is a through-bore which extends from end 178A to end 176A. In some embodiments, hole 180A is a channel arranged in blade portion 174A which extends from end 178A to end 176A. In some embodiments, hole 180A is a through-bore which extends from a point between end 178A and end 176A, to end 176A. In some embodiments, hole 180A is a channel arranged in blade portion 174A which extends from a point between end 178A and end 176A, to end 176A.

Blade portion 174B comprises end 176B and end 178B. As shown, blade portion 174A is telescopingly engaged with blade portion 174B (i.e., blade portion 174A slides within blade portion 174B). In some embodiments, blade portion 174A slides around blade portion 174B. Blade portion 174B further comprises hole 180B. Hole 180B is substantially aligned with hole 180A. Blade portion 174B further comprises flange 182 proximate end 176B. Flange 182 reduces the diameter of hole 180B in order to engage protrusions of the pivotable wire. Specifically, as pivotable wire 30, for example, is inserted into hole 180A from end 178A in longitudinal direction LD1, and subsequently into hole 180B, flange 182 allows section 44 and pivotable section 60 to extend at least partially out of hole 180B beyond end 176B, but allows only a portion of section 32 to do the same. As such, retractor blade 170, like section 32, is arranged to pivotably displace relative to section 44 and/or engaging portion 52. In some embodiments, retractor blade 170 comprises polycarbonate. In some embodiments, end 176B of retractor blade 170 is aligned with pivotable section 60 so that when section 44 and/or engaging portion 52 is engaged into disc or bone, retractor blade 170 (specifically end 176B) is held in firm apposition to the spine. This is to prevent tissue creep beneath end 176B of retractor blade 170 and consequent injury of retracted tissues from sharp surgical instruments. By firmly securing (e.g., screwing or impaling) section 44 and/or engaging portion 52 into bone or cartilage, it can firmly appose retractor blade 170 to the spine, but simultaneously allow infinite angle changes in retractor blade 170 by virtue of the swivel while preventing tissue creep beneath the blade which is common in present systems and aggravating as well as hazardous. In some embodiments, a plurality of pivotable wires are used, if desired, to fixate retractor blade 170 more securely, or to fixate end 176B in a particular rotator orientation referable to the vertical axis. In this regard, retractor blade 170 would or could have a plurality of holes (e.g., holes similar to or identical to holes 180A and 180B) to engage such fixations or pivotable wires. For example, two pivotable wires (e.g., pivotable wires 30) may be fed down two separate holes (e.g., two sets of holes 180A and 180B) and secured to a vertebra, which would provide greater stabilization and securement to the retractor blade (e.g., retractor blade 170), and limit the angular movement or rotation of the retractor blade.

Retractor blade 170 may further comprise button 184. Button 184 is operatively arranged to lock and unlock blade portion 174A with respect to blade portion 174B. For example, when button 184 is pressed, blade portion 174A is slidable with respect to blade portion 176B; when button 184 is released, blade portion 174A is locked with respect to blade portion 176B. Any suitable means for locking and unlocking may be used, for example, a pawl and gear system wherein button 184 releases and engages the pawl from the gears to unlock and lock, respectively, blade portion 174 with respect to blade portion 174B. In some embodiments, retractor blade 170 comprises polycarbonate.

Figure 9A:
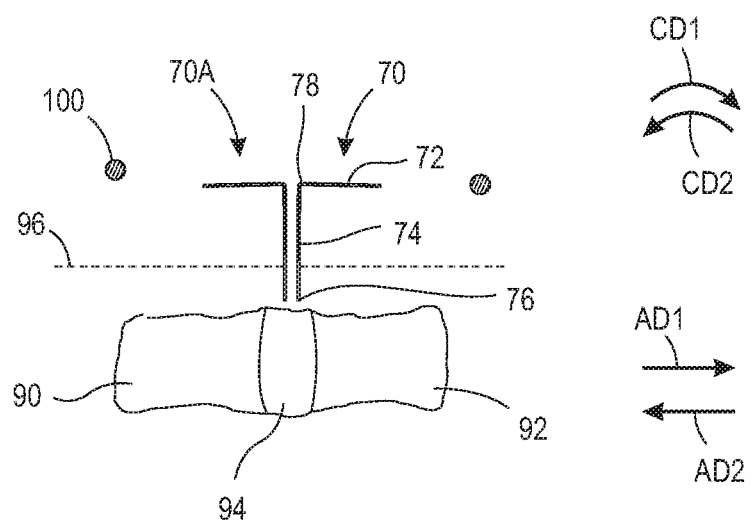
FIG. 9A is a side elevational view of retractor blades being inserted along a spine.

FIG. 9A is a side elevational view of retractor blades 70 and 70A being inserted along a spine having vertebra 90, vertebra 92, disc 94, and tissue 96. It should be appreciated that retractor blades 70A-C are substantially the same as retractor blade 70. For the purposes of this description only retractor blade 70 will be described. However, the same description is relevant to additional retractor blades 70A-C. As shown, end 76 of retractor blade 70 is inserted through tissue 96 until it abuts against or is arranged substantially proximate to disc 94. Tissue 96 may be, for example, psoas muscle. In some embodiments, end 76 is inserted through tissue 96 until it abuts against or is arranged substantially proximate to one of vertebrae 90 and 92. It should be further appreciated that any suitable pivotable wire may be used, for example, pivotable wire 30, 130, 230, 330.

Figure 9B:
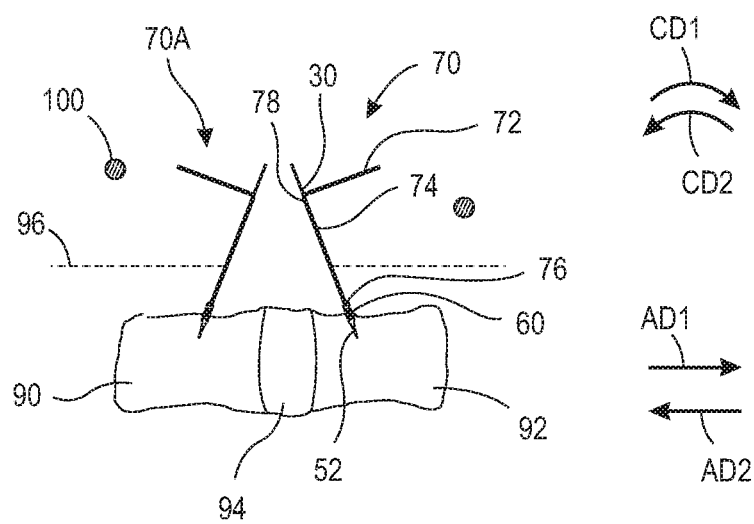
FIG. 9B is a side elevational view of the retractor blades displaced along the spine and mounted thereto.

FIG. 9B is a side elevational view of retractor blades 70 and 70A displaced along the spine and mounted thereto. As shown, end 76 is displaced in axial direction AD1 thereby displacing tissue 96 (i.e., pulling tissue 96 away from disc 94 and/or vertebra 92). Once end 76 is arranged at a suitable position about vertebra 92, pivotable wire 30 is inserted in end 78 and through hole 80 until engaging portion 52 extends at least partially out of end 76. Engaging portion 52 is then secured to vertebra 92 (e.g., by rotating pivotable wire 30 such that the threaded engaging portion 52 screws into vertebra 92 or by thrusting pivotable wire 30 toward the spine such that the sharpened engaging portion 52 impales into vertebra 92). The same process is followed with respect to retractor blade 70A and vertebra 90. The end of blade 70A is displaced in axial direction AD2 thereby displacing tissue 96 (i.e., pulling tissue 96 away from disc 94 and/or vertebra 90). Once in a suitable position, retractor blade 70A is secured to vertebra 90 via another pivotable wire 30.

Figure 9C:
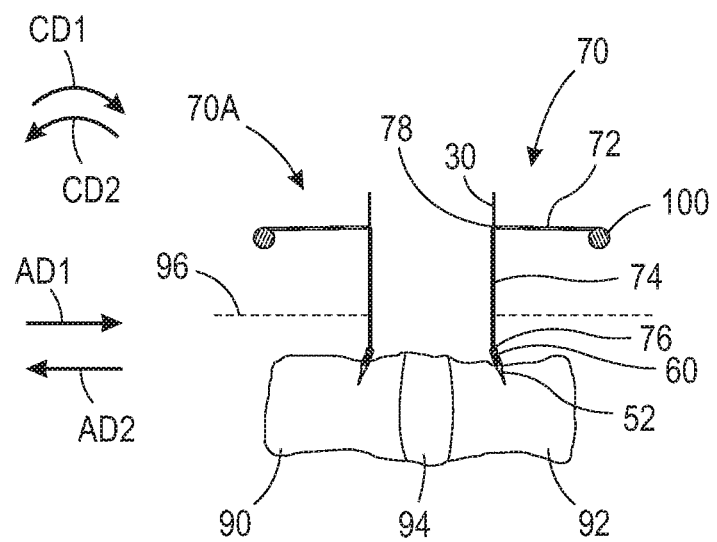
FIG. 9C is a side elevational view of the retractor blades mounted to a retractor blade mounting ring.

FIG. 9C is a side elevational view of retractor blades 70 and 70A mounted to retractor blade mounting ring 100. Once engaging portion 52 is secured to vertebra 92, retractor blade 70 is pulled away from vertebra 92 until flange 82 engages protrusions 38A-B (see FIG. 7) thereby exposing engaging portion and pivotable section. Retractor blade 70 is then rotated or pivoted in circumferential direction CD1 relative to engaging portion 52, thereby further displacing tissue 96. Handle portion 72 is then secured to retractor blade mounting ring 100. Retractor blade mounting ring 100 may be any suitable surgical retractor blade mount, such as a Bookwalter® retractor system. Retractor blade mounting ring 100 may comprise any suitable geometry, for example, a circular, ovular, ellipsoidal, triangular, rectangular, square, etc.-shaped geometry. Retractor blade mounting ring 100 may comprise a ratcheting device such that retractor blade 70 may be secured thereto, and ratcheted into position thus easing the force required by the user to retract tissue 96. Similarly, retractor blade 70A is rotated or pivoted in circumferential direction CD2 to displace tissue 96 and secured to retractor blade mounting ring 100 or a ratcheting device arranged thereon.

Figure 9D:
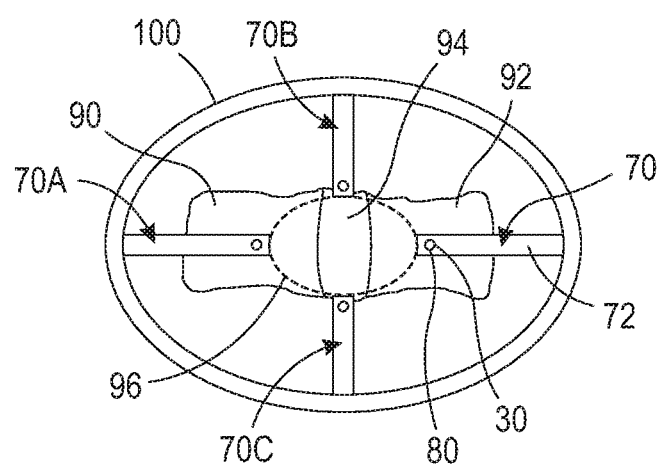
FIG. 9D is a top elevational view of the retractor blades mounted to the retractor blade mounting ring as shown in FIG. 9C.

FIG. 9D is a top elevational view of retractor blades 70 and 70A-C mounted to retractor blade mounting ring 100. Retractor blades 70 and 70A are pivotably connected to vertebrae 92 and 90, respectively, with pivotable wires 30 and secured to retractor blade mounting ring 100, thereby displacing tissue 96 and exposing disc 94 as shown. Any number of additional retractor blades, for example retractor blades 70B-C, may be used to further expose disc 94 or the area in which the user intends to access or view.

Figure 10A:
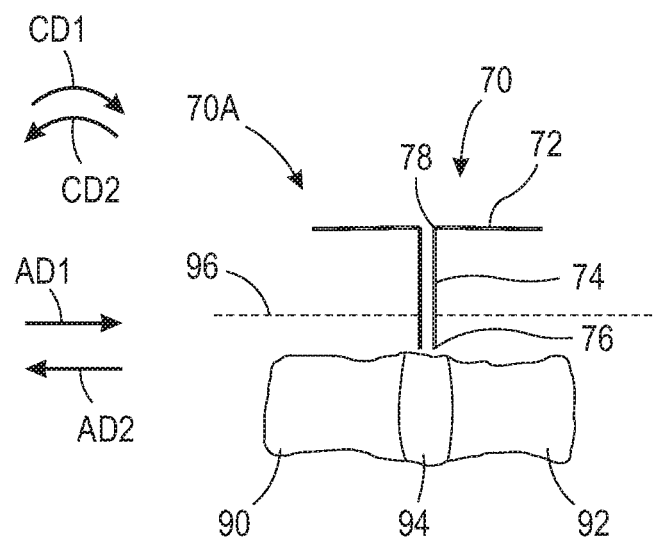
FIG. 10A is a side elevational view of retractor blades being inserted along a spine.

FIG. 10A is a side elevational view of retractor blades 70 and 70A being inserted along a spine having vertebra 90, vertebra 92, disc 94, and tissue 96. It should be appreciated that retractor blades 70A-C are substantially the same as retractor blade 70. For the purposes of this description only retractor blade 70 will be described. However, the same description is relevant to additional retractor blades 70A-C. As shown, end 76 of retractor blade 70 is inserted through tissue 96 until it abuts against or is arranged substantially proximate to disc 94. Tissue 96 may be, for example, psoas muscle. In some embodiments, end 76 is inserted through tissue 96 until it abuts against or is arranged substantially proximate to one of vertebrae 90 and 92. It should be further appreciated that any suitable pivotable wire may be used, for example, pivotable wire 30, 130, 230, 330.

Figure 10B:
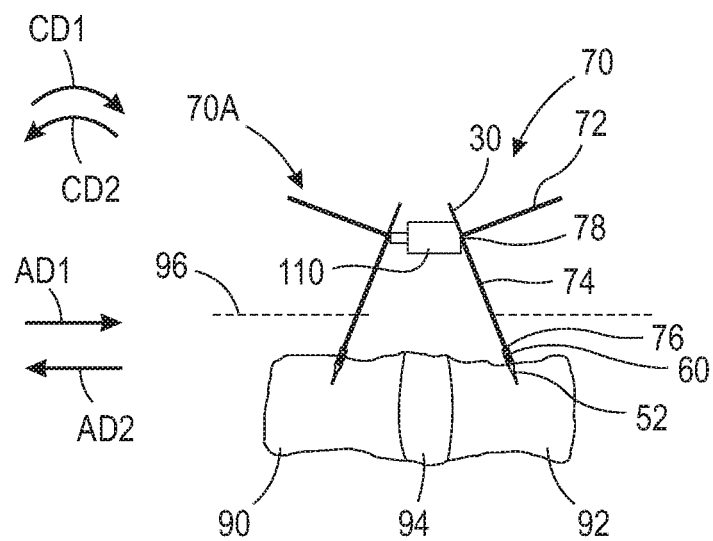
FIG. 10B is a side elevational view of the retractor blades displaced along the spine and mounted thereto.

FIG. 10B is a side elevational view of retractor blades 70 and 70A displaced along the spine and mounted thereto. As shown, end 76 is displaced in axial direction AD1 thereby displacing tissue 96 (i.e., pulling tissue 96 away from disc 94 and/or vertebra 92). Once end 76 is arranged at a suitable position about vertebra 92, pivotable wire 30 is inserted in end 78 and through hole 80 until engaging portion 52 extends at least partially out of end 76. Engaging portion 52 is then secured to vertebra 92 (e.g., by rotating pivotable wire 30 such that the threaded engaging portion 52 screws into vertebra 92 or by thrusting pivotable wire 30 toward the spine such that the sharpened engaging portion 52 impales into vertebra 92). The same process is followed with respect to retractor blade 70A and vertebra 90. The end of blade 70A is displaced in axial direction AD2 thereby displacing tissue 96 (i.e., pulling tissue 96 away from disc 94 and/or vertebra 90). Once in a suitable position, retractor blade 70A is secured to vertebra 90 via another pivotable wire 30. Expansion mechanism 110 may be positioned between retractor blades 70 and 70A. In some embodiments, handle portion 72 may be removed from blade portion 74.

Figure 10C:
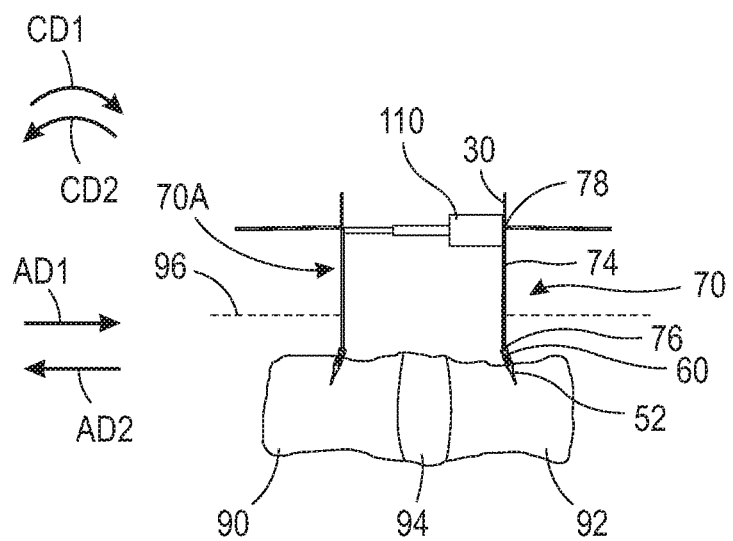
FIG. 10C is a side elevational view of the retractor blades expanded via an expansion mechanism; and, FIG. 10D is a top elevational view of the retractor blades expanded via the expansion mechanism as shown in FIG. 10D.

FIG. 10C is a side elevational view of retractor blades 70 and 70A expanded via expansion mechanism 110. Once engaging portion 52 is secured to vertebra 92, retractor blade 70 is pulled away from vertebra 72 until flange 82 engages protrusions 38A-B (see FIG. 7) thereby exposing engaging portion and pivotable section. Retractor blade 70 is then rotated or pivoted via expansion mechanism 110 in circumferential direction CD1 relative to engaging portion 52, thereby further displacing tissue 96. Similarly, retractor blade 70A is rotated or pivoted via expansion mechanism 110 in circumferential direction CD2 to displace tissue 96 and secured to retractor blade mounting ring 100 or a ratcheting device arranged thereon. As shown, expansion mechanism 110 is positioned between retractor blades 70 and 70A and expanded thus, at the same time, rotating retractor blade 70 in circumferential direction CD1 and retractor blade 70A in circumferential direction CD2. Expansion mechanism 110 may comprise a ratcheting device thus easing the force required by the user to retract tissue 96. Expansion mechanism 110 may comprise any suitable device for forcing retractor blades 70 and 70A apart, such as a hydraulic piston, threaded jack, ratcheting jack, etc.

Figure 10D:
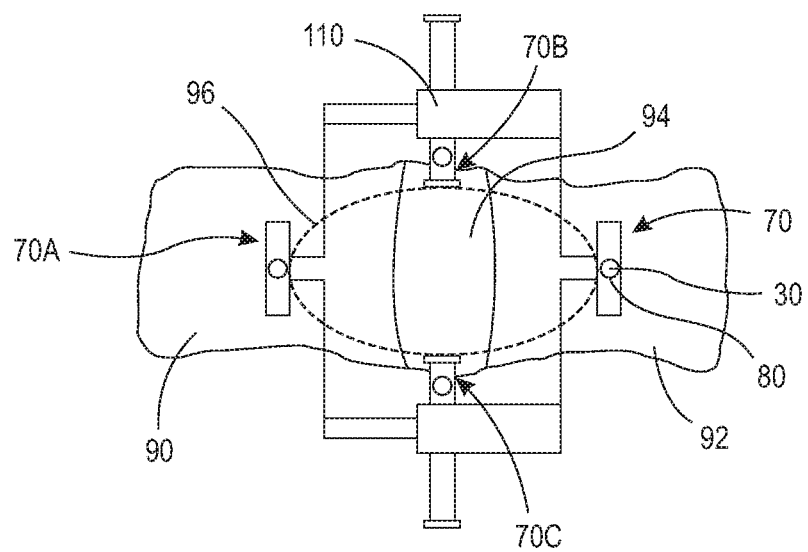

FIG. 10D is a top elevational view of retractor blades 70 and 70A-C expanded via expansion mechanism 110. Retractor blades 70 and 70A are pivotably connected to vertebrae 92 and 90, respectively, with pivotable wires 30 and secured to the expanded expansion mechanism 110, thereby displacing tissue 96 and exposing disc 94 as shown. Any number of additional retractor blades, for example retractor blades 70B-C, may be used to further expose disc 94 or the area in which the user intends to access or view.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

10 Pivotable wire assembly (or pivotable K-wire assembly)
12 Retractor blade assembly
20 Sheath
22 End
24 End
26A Slot
26B Slot
28A Edge
28B Edge (not shown)
30 Pivotable wire (or pivotable K-wire)
32 Section
34 End
36 End
38A Protrusion
38B Protrusion
40 Fork
42 Pin
44 Section
46 Fork
48 Center block
50 Pin
52 Engaging portion
60 Pivotable section
70 Retractor blade
70A Retractor blade
70B Retractor blade
70C Retractor blade
72 Handle portion
74 Blade portion
76 End
78 End
80 Hole
82 Flange
90 Vertebra
92 Vertebra
94 Disc
96 Tissue
100 Retractor blade mounting ring
110 Expansion mechanism
130 Pivotable wire (or pivotable K-wire)
132 Section
134 End
136 End
138A Protrusion
138B Protrusion
140 Ball
142 Section
144 Socket
146 Engaging portion
160 Pivotable section
170 Retractor blade
172 Handle portion
174 Blade portion
174A Blade portion
174B Blade portion
176A End
176B End
178A End
178B End
180A Hole
180B Hole 182 Flange
184 Button
230 Pivotable wire (or pivotable K-wire)
232 Section
234 End
236 End
238A Protrusion
238B Protrusion
240 Knuckle
242 Section
244 Knuckle
246 Knuckle
248 Pin
250 Engaging portion
260 Pivotable section
330 Pivotable wire (or pivotable K-wire)
332 Section
334 End
336 End
338A Protrusion
338B Protrusion
340 Section
342 Engaging portion
360 Pivotable section
D1 Diameter
D2 Diameter
D3 Diameter
LD1 Longitudinal direction
LD2 Longitudinal direction
AD1 Axial direction
AD2 Axial direction
RD1 Radial direction
RD2 Radial direction

What is claimed is:

1. A pivotable wire assembly, comprising:
a pivotable wire, including:
a first section having a first end and a second end;
a pivotable section; and,
a second section connected to the second end via the pivotable section, the second section having an engaging portion; and,
a sheath having a third end and a fourth end, the sheath operatively arranged to be removably engaged around the pivotable wire;
wherein:
the first section is pivotably displaceable relative to the second section; and,
when the sheath is fully engaged with the pivotable wire, at least a portion of the first section, the pivotable section, at least a portion of the second section, and at least a portion of the engaging portion is arranged within the sheath.

2. The pivotable wire assembly as recited in claim 1, wherein the first section further comprises one or more protrusions arranged proximate the second end.

3. The pivotable wire assembly as recited in claim 2, wherein the sheath comprises one or more slots, wherein the one or more slots are arranged to engage the one or more protrusions.

4. The pivotable wire assembly as recited in claim 2, further comprising a retractor blade, the retractor blade including:
a fifth end;
a sixth end; and,
a hole.

5. The pivotable wire assembly as recited in claim 4, wherein the hole extends from the fifth end to the sixth end.

6. The pivotable wire assembly as recited in claim 5, wherein retractor blade further comprises a flange at least partially aligned with the hole proximate the sixth end, the flange being operatively arranged to engage the one or more protrusions.

7. The pivotable wire assembly as recited in claim 2, further comprising a retractor blade, the retractor blade including:
a first blade portion; and,
a second blade portion connected to and slidable with respect to the first blade portion.

8. The pivotable wire assembly as recited in claim 7, wherein the retractor blade further comprises a button operatively arranged to lock and unlock the first blade portion with respect to the second blade portion.

9. The pivotable wire assembly as recited in claim 1, wherein, when the sheath is fully engaged with the pivotable wire, the first section, the second section, and the engaging portion are substantially concentrically aligned.

10. The pivotable wire assembly as recited in claim 1, wherein the pivotable section comprises a universal joint.

11. The pivotable wire assembly as recited in claim 1, wherein:
the first section further comprises a first fork connected to the second end;
the second section further comprises a second fork connected to the engaging portion; and,
the first fork and the second fork are pivotably connected to a center block.

12. The pivotable wire assembly as recited in claim 1, wherein the pivotable section comprises a ball and socket joint.

13. The pivotable wire as recited in claim 1, wherein:
the first section further comprises a ball connected to the second end;
the second section further comprises a socket connected to the engaging portion; and,
the ball is pivotably engaged with the socket.

14. The pivotable wire assembly as recited in claim 1, wherein the pivotable section comprises a hinged joint.

15. The pivotable wire as recited in claim 1, wherein:
the first section further comprises a first knuckle connected to the second end;
the second section further comprises a second knuckle connected to the engaging portion; and,
the first knuckle is hingedly connected to the second knuckle.

16. The pivotable wire assembly as recited in claim 1, wherein:
the first section comprises a first diameter;
the second section comprises a second diameter; and,
the pivotable section comprises a third diameter, the third diameter being less than the first diameter and the second diameter.

17. The pivotable wire assembly as recited in claim 1, wherein the engaging portion comprises threading.

18. A retractor blade assembly, comprising:
a retractor blade, including:
a blade portion having a first end, a second end, a hole, and a flange extending at least partially into the hole proximate the second end; and,
a handle portion connected to the blade portion proximate the first end; and, a pivotable wire operatively arranged to engage the hole, the pivotable wire including:
a first section having a third end, a fourth end, and one or more protrusions arranged proximate the fourth end, wherein the flange is operatively arranged to engage the one or more protrusions;
a pivotable section; and,
a second section connected to the fourth end via the pivotable section, the second section having an engaging portion;
wherein the first section is pivotably displaceable relative to the second section.

19. A pivotable wire assembly, comprising:
a pivotable wire, including:
    a first section having a first end and a second end;
    a pivotable section; and,
    a second section connected to the second end via the pivotable section, the second section having an engaging portion; and,
a sheath component having a third end and a fourth end, the sheath component operatively arranged to be removably engaged around the pivotable wire;
wherein:
    the first section is pivotably displaceable relative to the second section; and,
    when the sheath component is fully engaged with the pivotable wire, the first section, the second section, and the engaging portion are substantially concentrically aligned.

20. The pivotable wire assembly as recited in claim 19, wherein the first section further comprises one or more protrusions arranged proximate the second end.

21. The pivotable wire assembly as recited in claim 20, wherein the sheath component comprises one or more slots, wherein the one or more slots are arranged to engage the one or more protrusions.

22. The pivotable wire assembly as recited in claim 19, wherein the sheath component is a retractor blade.

\* \* \* \* \*